US010019565B2

(12) United States Patent
Ewing

(10) Patent No.: US 10,019,565 B2
(45) Date of Patent: Jul. 10, 2018

(54) METHOD OF AUTHENTICATING INTEGRATED CIRCUITS USING OPTICAL CHARACTERISTICS OF PHYSICALLY UNCLONABLE FUNCTIONS

(71) Applicant: Honeywell Federal Manufacturing & Technologies, LLC, Kansas City, MO (US)

(72) Inventor: Daniel Jonathan Ewing, Overland Park, KS (US)

(73) Assignee: Honeywell Federal Manufacturing & Technologies, LLC, Kansas City, MO (US)

( * ) Notice: Subject to any disclaimer, the term of this patent is extended or adjusted under 35 U.S.C. 154(b) by 208 days.

(21) Appl. No.: 14/973,383

(22) Filed: Dec. 17, 2015

(65) Prior Publication Data

US 2017/0177853 A1    Jun. 22, 2017

(51) Int. Cl.
| | |
|---|---|
| *G06F 21/44* | (2013.01) |
| *H01L 23/00* | (2006.01) |
| *G06F 21/45* | (2013.01) |
| *G01N 21/66* | (2006.01) |
| *G01N 21/64* | (2006.01) |

(52) U.S. Cl.
CPC ......... *G06F 21/44* (2013.01); *G01N 21/6489* (2013.01); *G01N 21/66* (2013.01); *G06F 21/45* (2013.01); *H01L 23/576* (2013.01); *G01N 2201/12* (2013.01)

(58) Field of Classification Search
CPC ................................. G06F 21/44; G06F 21/45
See application file for complete search history.

(56) References Cited

U.S. PATENT DOCUMENTS

| | | | |
|---|---|---|---|
| 4,755,049 A | 7/1988 | Bomback | |
| 4,840,816 A | 6/1989 | Appleton | |
| 8,741,713 B2 * | 6/2014 | Bruley | H01L 22/34 257/639 |
| 8,848,905 B1 | 9/2014 | Hamlet et al. | |
| 2006/0095773 A1 | 5/2006 | Itoh | |
| 2008/0231418 A1 | 9/2008 | Ophey | |
| 2015/0215115 A1 | 7/2015 | Pikus | |

FOREIGN PATENT DOCUMENTS

| | | |
|---|---|---|
| WO | WO2005048179 | 5/2005 |
| WO | WO2012038842 | 3/2012 |

* cited by examiner

*Primary Examiner* — Tony Ko
(74) *Attorney, Agent, or Firm* — Hovey Williams LLP

(57) ABSTRACT

A method and apparatus for reading unique identifiers of an integrated circuit. The unique identifiers may be physically unclonable functions (PUFs), formed by high energy ions implanted into semiconductor material of the integrated circuit. The method may include electrically or optically stimulating each of the PUFs and sensing with an optical sensor optical characteristics of resulting light emitted from the PUFs. Then the method may include comparing values associated with the optical characteristics of the PUFs with groups of stored values in a circuit database. Each of the groups of stored values may be associated with optical characteristics of PUFs of a known authentic circuit. The method may then include the controller providing verification of authenticity of the integrated circuit when each of the values associated with the optical characteristics of the PUFs match the stored values of at least one of the groups in the circuit database.

18 Claims, 3 Drawing Sheets

METHOD OF AUTHENTICATING INTEGRATED CIRCUITS USING OPTICAL CHARACTERISTICS OF PHYSICALLY UNCLONABLE FUNCTIONS

BACKGROUND

Detecting counterfeit electronics, such as integrated circuits, is an important challenge facing many companies, because such counterfeiting can cause significant economic losses. Unfortunately, detecting counterfeit integrated circuits is difficult because such circuits are mounted inside electronic devices.

One anti-counterfeit method uses an electrical process in which variations in fabrication of the circuit lead to variations in electrical properties. These variations, often referred to as physically unclonable functions (PUFs), are then used as identifiers. Unfortunately, these PUFs require operation of the integrated circuit device in order to function properly. This, in turn, requires fabrication of a complex integrated circuit, thus making it obvious to non-authorized entities that the device has been identified as important enough to protect. Another disadvantage of these types of PUFs is that they can only be used in Si CMOS circuits, due to the digital circuitry and memory requirements for identification of these PUFs.

Thus, there is a need for a simplified and more discreet method of verifying the authenticity of integrated circuits.

SUMMARY OF THE INVENTION

Embodiments of the present invention solve the above-mentioned problems and provide a distinct advance in the art of verifying the authenticity of integrated circuits.

One embodiment of the invention is a method of reading unique identifiers of an integrated circuit to detect authenticity of the circuit. The unique identifiers may be physically unclonable functions (PUFs). Specifically, the PUFs may include high energy ions implanted into crystal lattices of semiconductor material of the integrated circuit at a plurality of locations, each location forming one of the PUFs having unique associated damage. The method may include a step of electrically or optically stimulating each of the PUFs and sensing with an optical sensor optical characteristics of light emitted from the PUFs when optically stimulated. Then the method may include a step of comparing values associated with the optical characteristics of the PUFs with one or more groups of stored values in a circuit database. Each of the groups of stored values in the circuit database may be associated with optical characteristics of PUFs of a known authentic circuit. The method may further include a step of providing verification of authenticity of the integrated circuit when each of the values associated with the optical characteristics of the PUFs match the stored values of at least one of the groups in the circuit database.

In some embodiments of the invention, the optical characteristics of the PUFs of the integrated circuit may include wavelength, intensity, and/or total area of the light received with the optical sensor from each of the PUFs of the integrated circuit. The step of providing verification of authenticity may include providing an audible or visual indication of the authenticity of the integrated circuit. Furthermore, in some embodiments of the invention, the method may further include a step of providing an audible or visual indication that the integrated circuit is a counterfeit circuit when each of the values associated with the optical characteristics of the PUFs do not match the stored values of at least one of the groups in the circuit database.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the current invention are described in detail below with reference to the attached drawing figures, wherein.

Figure 1:
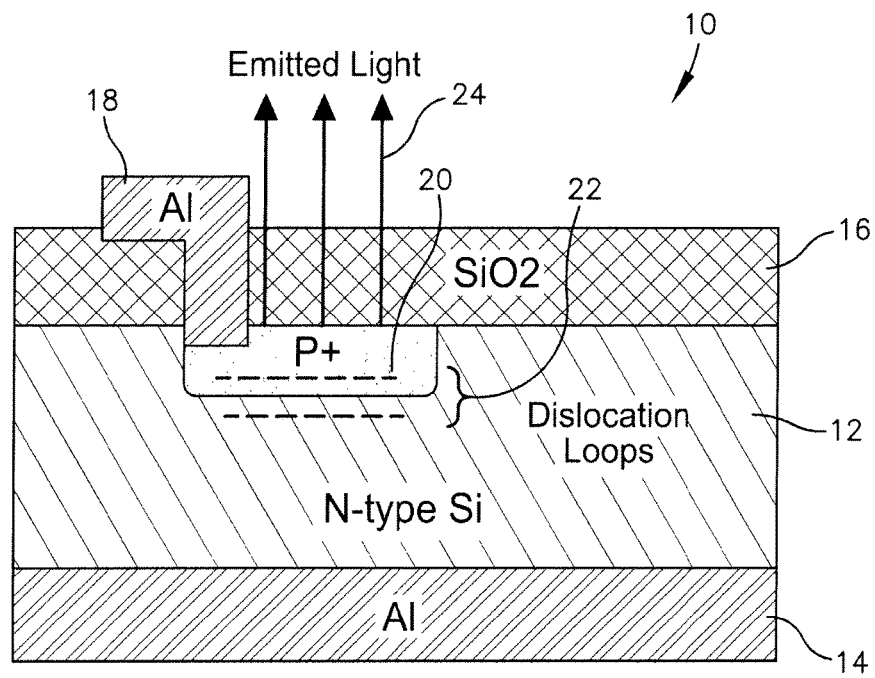
FIG. 1 is a schematic cross-sectional view of an integrated circuit constructed according to embodiments of the present invention, illustrating light emitting from a dislocation loop area.

The drawing figures do not limit the current invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the current invention. The following detailed description is, therefore, not to be taken in a limiting sense. The scope of the current invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

Embodiments of the invention, illustrated in FIGS. 1-5, include an authentication apparatus 28 and method for detecting and deciphering unique identifiers on an integrated circuit 10. As illustrated in FIG. 1, the integrated circuit 10 may comprise one or more semiconductor materials 12 such as any combination of Si, SiGe, GaAs, and/or GaN. In some embodiments of the invention, the semiconductor materials 12 may have a conductive metal 14 such as aluminum or other conductive materials known in the art applied to the bottom of the semiconductor materials 12 and may have one or more layers of a dielectric material 16, such as silicon dioxide ($SiO_2$) applied over the semiconductor materials 12, as illustrated in FIG. 1. Note that aluminum and other conductive metals may also be used at other locations on the integrated circuit 10, forming various electrical devices 18, components, and connections thereon.

The semiconductor materials 12 may include crystal lattices into which high energy ions 20 may be implanted during integrated circuit fabrication. The ions 20 implanted into the crystal lattices may include, for example, boron and/or phosphorus, as illustrated in FIG. 1. Defect areas created by this ion implantation may include amorphous regions. After annealing, the amorphous regions may recrystallize, with a large number of line defects or dislocation loops 22. These dislocation loops 22 may be responsible for emitting light 24 having specific emission spectra when electrically or optically stimulated, as described below.

Figure 2:
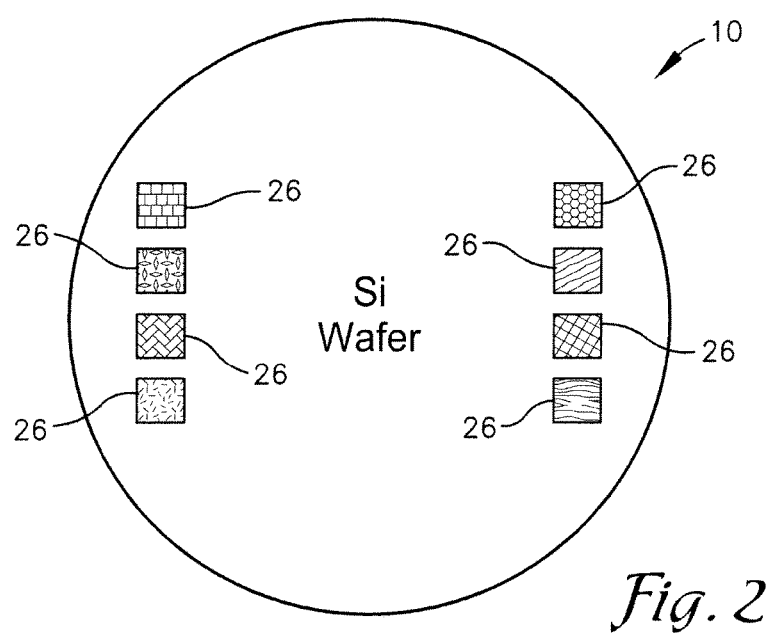
FIG. 2 is a top view of the integrated circuit of FIG. 1, illustrating ion implant regions or physically unclonable functions (PUFs) with varying material properties.

As illustrated in FIG. 2, the integrated circuit 10 may include a plurality of locations at which the high energy ions 20 are implanted. At each of these locations, the implanted ions 20 may form areas of defect which can emit light, similar to a micro-scale light emitting diode (LED), when electrically or optically stimulated. Specifically, the resulting damage at each of these locations may be referred to herein as unique identifiers or physically unclonable functions (PUFs) 26. The PUFs 26 are represented in FIG. 2 with different patterns representing small random changes in material properties due to varying acceleration energy, ion dose, and/or beam size used in the creation of the PUFs 26. These resulting material variations can include ion implant concentration, how many atoms are implanted, ion implant depth, number of dislocation loops 22, and/or a size of an area that is implanted for each of the PUFs 26. Dislocation loops 22 may be defined herein as line defects in the semiconductor material 12, or an extra line of atoms inserted between two other lines of atoms and completely contained in the crystal lattice. The higher the dose or the higher the acceleration energy used during ion implantation, the more dislocation loops 22 created.

At least some of the PUFs 26 on the integrated circuit 10 may have differing optical properties than others when electrically or optically stimulated, resulting in electroluminescence or photoluminescence, based on their differing material properties described above. The resulting intensity, wavelength, or any other optical properties of the light 24 emitted by the PUFs 26 may be logged or recorded in a database for later verification of the authenticity of the integrated circuit 10. For example, the plurality of locations implanted with PUFs 26 may include sixty-four discrete areas, cooperatively providing a sixty-four digit key serving as a circuit authentication identifier for the circuit 10. In FIG. 2, eight PUFs 26 are illustrated, each of which may represent specific values and/or specific optical properties measured and stored in a database for a particular manufacturer or authentication agency.

In some embodiments of the invention, the implantation of the ions 20 to form the PUFs 26 may be performed by an ion implantation device (not shown). The ion implantation device may include standard semiconductor fabrication tools known in the art, such as an ion implanter, focused ion beam tools, or any other device(s) known in the art for creating small random changes in material properties of the circuit's crystal lattice. Furthermore, the ion implantation device may be configured to manually of automatically vary acceleration energy, ion dose, and/or beam size in order to vary the resulting material properties of the PUFs 26 to be measured and identified, as later described herein.

Figure 3:
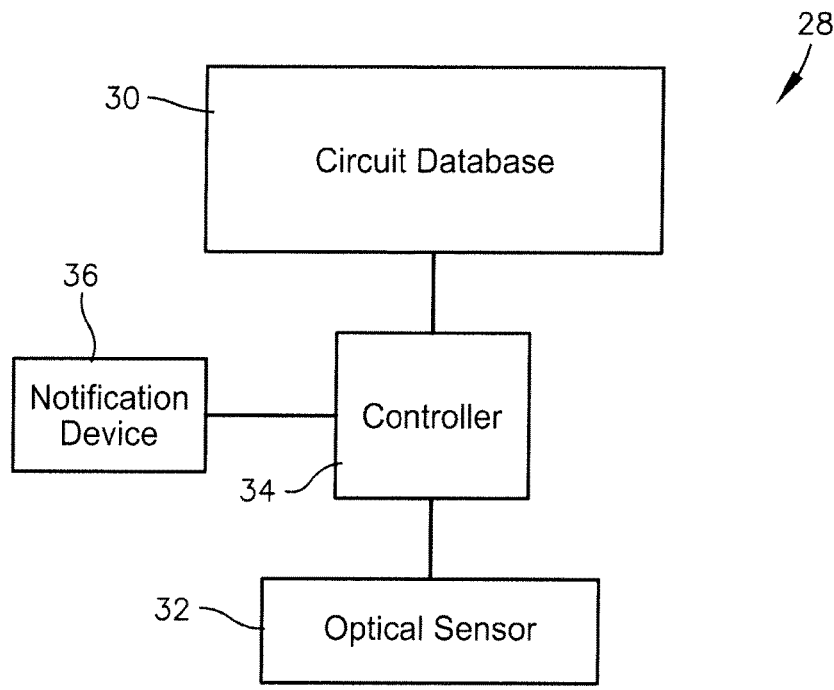
FIG. 3 is a block diagram of an authentication apparatus for analyzing light emitted from the PUFs.

Some embodiments of the invention, as illustrated in FIG. 3, may include an authentication apparatus 28 configured to document the PUFs 26 and/or authenticate the integrated circuit 10 using PUF data stored in a circuit database 30. The authentication apparatus 28 may include an optical sensor 32, the circuit database 30, and/or a controller 34 configured to receive optical measurements from the optical sensor 32 and to compare those measurements with circuit authentication information stored in the circuit database 30.

The optical sensor 32 may be any one or more sensors configured to measure an amount of light intensity and wavelength emitted from the PUFs 26. For example, the PUFs 26 may emit light via electroluminescence (i.e., emitting light in response to the passage of an electric current or to a strong electric field) or photoluminescence (emitting light in response to photoexcitation of photons in the PUFs). One or more energy sources (not shown) configured for creating the electroluminescence or photoluminescence described above may be used in conjunction with the optical sensor 32 and/or may be integrated into a housing of the optical sensor 32. In use, the optical sensor 32 may be positioned relative to the circuit 10 in a location close enough to receive and quantify the light 24 emitted from the PUFs 26 when stimulated electrically or optically. The optical sensor 32 may also be communicatively coupled with the controller 34, to send information related to the emitted light 26 back to the controller 34 to be analyzed.

The circuit database 30, as illustrated in FIG. 3, may comprise residential or external memory that may be integral with the controller 34, stand-alone memory, or a combination of both. The memory may include, for example, removable and non-removable memory elements such as RAM, ROM, flash, magnetic, optical, USB memory devices, MMC cards, RS MMC cards, SD cards such as microSD or miniSD, SIM cards, and/or other memory elements. The circuit database 30 may store, for example, keys, codes, variables, or other values corresponding to optical properties and/or material properties of the PUFs 26 of one or more circuits. These stored values may include values associated with intensity of the emitted light 24, wavelength of the emitted light 24, and/or a size of an area that is implanted with the ions 20.

The controller 34 may comprise any number of combination of processors, circuits, integrated circuits, programmable logic devices such as programmable logic controllers (PLC) or motion programmable logic controllers (MPLC), computers, processors, microcontrollers, transmitters, receivers, other electrical and computing devices, and/or residential or external memory for storing data and other information about the optical sensor 32 and/or the PUFs 26. The controller 34 may control operation of the optical sensor 32 and/or receive signals corresponding to light 24 sensed thereby, including intensity and wavelength measurements to be stored in the circuit database 30 during the manufacturing stage and then later compared to values stored in the circuit database 30 to determine authenticity of the circuit 10.

The controller 34 may be configured to implement any combination of algorithms, subroutines, computer programs, or code corresponding to method steps and functions described herein. The controller 34 and computer programs described herein are merely examples of computer equipment and programs that may be used to implement the present invention and may be replaced with or supplemented with other controllers and computer programs without departing from the scope of the present invention. While certain features are described as residing in the controller 34, the invention is not so limited, and those features may be implemented elsewhere. For example, one or more of the circuit databases 30 may be remotely accessed by the controller 34 for retrieving PUF-related measurements without departing from the scope of the invention.

The controller 34 may implement the computer programs and/or code segments to perform various method steps described herein. The computer programs may comprise an ordered listing of executable instructions for implementing logical functions in the controller. The computer programs can be embodied in any computer-readable medium for use by or in connection with an instruction execution system, apparatus, or device, and execute the instructions. In the context of this application, a "computer-readable medium" can be any physical medium that can contain, store, communicate, propagate, or transport the program for use by or in connection with the instruction execution system, apparatus, or device. The computer-readable medium can be, for example, but not limited to, an electronic, magnetic, optical, electro-magnetic, infrared, or semi-conductor system, apparatus, or device. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), a portable compact disk read-only memory (CDROM), an optical fiber, multi-media card (MMC), reduced-size multi-media card (RS MMC), secure digital (SD) cards such as microSD or miniSD, and a subscriber identity module (SIM) card.

In some embodiments of the invention, the authentication apparatus 28 may further comprise and/or be communicably coupled with a notification device 36, such as a user interface, visual display device, and/or speaker, any of which may communicate to a user, visually or audibly. For example, the visual display device may be a computer screen or may simply be one or more LEDs configured to visually indicate if the integrated circuit 10 is determined by the controller 34 to be authentic or counterfeit. Additionally or alternatively, the speaker may be configured to output an audible indication to the user regarding the authenticity of the integrated circuit 10. In some embodiments of the invention, the notification device 36 may further include a wireless transmitter configured to transmit information from the controller 34 to a remote notification device, such as another computer, tablet, smart phone, or the like.

In use, the integrated circuit 10 may be tagged and identified at the wafer scale during fabrication. For example, the authentication apparatus 28 may measure and record optical characteristics of the circuit 10 in the circuit database 30. Then, to later verify the authenticity of the circuit 10, the authentication apparatus 28 may again measure the optical characteristics of the circuit 10 and compare those optical characteristics to those earlier recorded and stored in the circuit database 30. The authentication apparatus 28 may then communicate to a user whether or not the circuit 10 is authentic or is a counterfeit circuit. That is, if the optical characteristics measured do not correspond with any of the measurements recorded or otherwise stored in the circuit database 30, the authentication apparatus 28 may identify the circuit 10 as a counterfeit.

Figure 4:
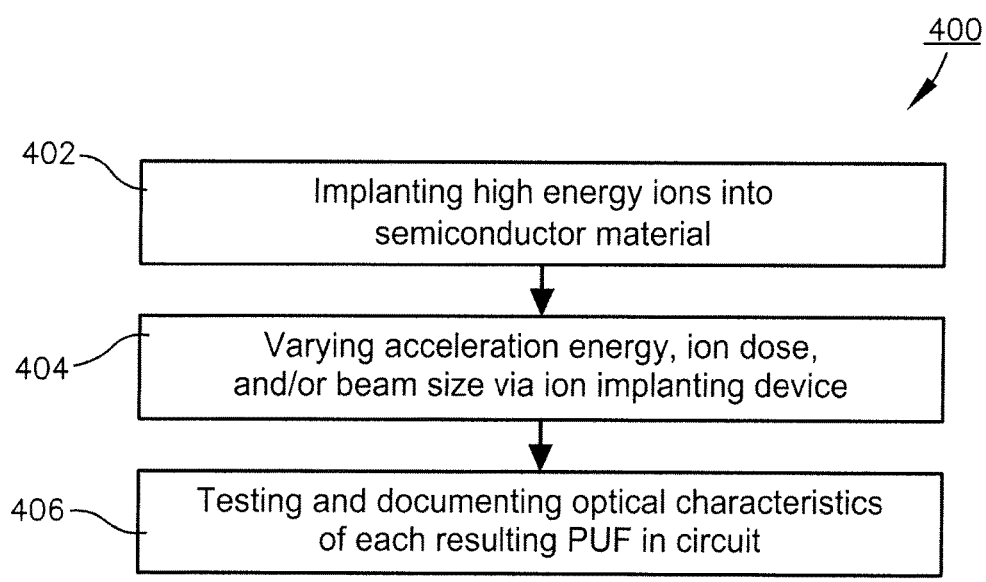
FIG. 4 is a flow chart illustrating a method of marking an integrated circuit with PUFs in accordance with embodiments of the present invention.
Figure 5:
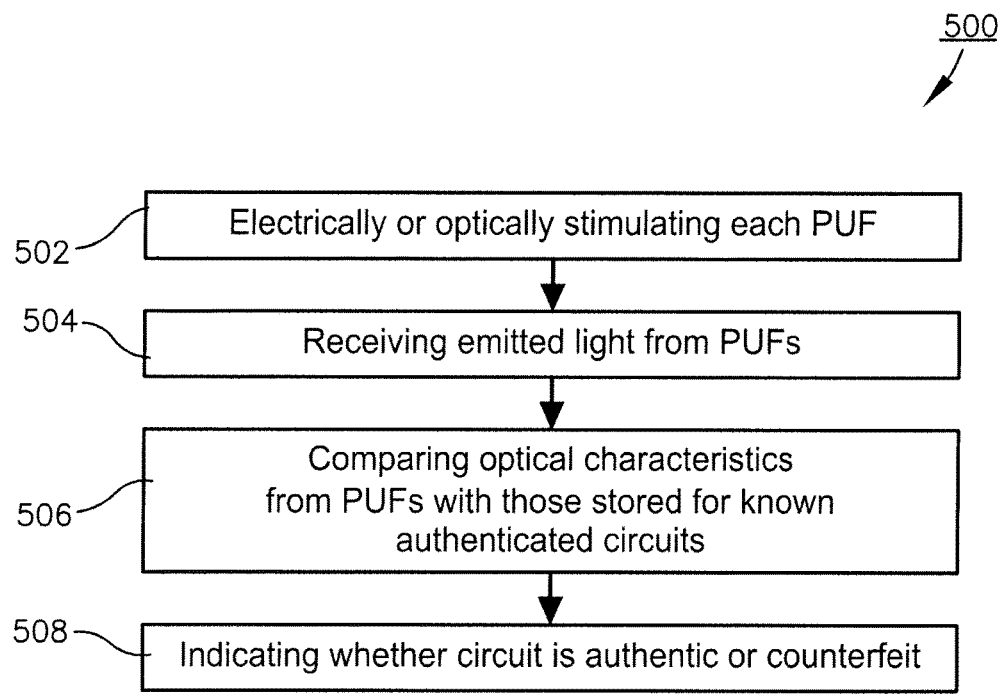
FIG. 5 is a flow chart illustrating a method of detecting and deciphering PUFs on the integrated circuit in accordance with embodiments of the present invention.

Method steps for marking and/or identifying unique identifiers or PUFs 26 on the integrated circuits 10 will now be described in more detail, in accordance with various embodiments of the present invention. The steps of the methods 400 and 500 may be performed in the order as shown in FIGS. 4 and 5, or they may be performed in a different order. Furthermore, some steps may be performed concurrently as opposed to sequentially. In addition, some steps may not be performed.

As illustrated in FIG. 4, the method 400 of marking circuits, such as the integrated circuit 10, with unique identifiers or PUFs may include a step of implanting the high energy ions 20 into crystal lattices of the semiconductor material 12 of the circuit 10 at a plurality of locations using ion implanters and/or focused ion beam tools, as depicted in block 402. This may be done to improve conductivity of certain regions, to isolate devices of the circuit 10 from each other, and/or to intentionally create the PUFs 26 described herein. Because of slight variations in the fabrication process, each resulting defect center or PUF 26 is unique, with a specific light emission intensity and wavelength. Thus, at least some of the PUFs 26 may have differing optical properties than others of the PUFs 26 when electrically or optically stimulated. In the integrated circuit 10 depicted in FIG. 2, eight discrete areas of damage may be associated with an eight-digit key serving as a circuit authentication identifier. However, in another embodiment of the invention, the plurality of locations implanted with PUFs 26 may include sixty-four discrete areas, cooperatively providing a sixty-four digit key serving as the circuit authentication identifier for that circuit. Any number of PUFs 26 may be formed on the integrated circuit 10 without departing from the scope of the invention.

In some embodiments of the invention, the method 400 may also include a step of varying acceleration energy, ion dose, and/or beam size used for creation of the PUFs 26, as depicted in block 404, thereby affecting how deep the ions 20 are implanted, how many atoms are implanted, and/or a size of an area that is implanted for each of the PUFs 26. These characteristics of the PUFs 26 may in turn affect intensity and wavelength output by these PUFs 26 when optically stimulated. Furthermore, the method 400 may include a step of testing and documenting optical characteristics of the PUFs 26 for each circuit, as depicted in block 406. For example, for each known authentic circuit, a group of values associated with optical characteristics of PUFs of that known authentic circuit may be stored in the circuit database 30. Additionally or alternatively, intensity and wavelength measurements for each of the PUFs 26 may be determined and stored in the circuit database 30 for a particular company, industry, or agency, to be looked up for later authentication.

As illustrated in FIG. 5, the method 500 of detecting and deciphering the unique identifiers or PUFs 26 on the circuits, such as the integrated circuit 10, may include the steps of electrically or optically stimulating each of the PUFs 26, as depicted in block 502, and sensing with the optical sensor 32 optical characteristics of light 24 emitted from the PUFs 26 when electrically or optically stimulated, as depicted in block 504. This may be done automatically via commands from the controller 34 or may be accomplished manually by a user shining light and positioning the optical sensor 32 at a desired location relative to the circuit 10 to detect the PUFs 26. Note that some manufacturers may chose a specific region on the circuits in which to implant the ions 20 forming these PUFs 26. Thus, authorizing personnel and/or the authentication apparatus 28 would be provided information regarding where the light source and/or the optical sensor 32 must be placed in relation to these PUFs 26 in order to properly measure their optical properties.

Next, the method 500 may include a step of comparing values associated with the optical characteristics of the PUFs 26 with one or more groups of stored values in the circuit database 30, as depicted on block 506. For example, the comparing step 506 may include determining a wavelength, intensity, and/or total area of light received with the optical sensor 32 from each of the PUFs 26, and then assigning a value to each of the PUFs based on those optical characteristics. This value may be assigned based on an algorithm solved using one or more of those optical characteristics or based on a look-up table using one or more of those optical characteristics. In one example embodiment of the invention, if the intensity of a given PUF 26 is above a predetermined threshold value, that PUF 26 may be assigned the numeral 1, but if the intensity is below the predetermined threshold value, that PUF 26 may be assigned to the numeral 0. The resulting string of 1's and 0's thus associated with the PUFs 26 of the circuit 10 may then be compared to a plurality of strings of 1's and 0's stored in the circuit database 30 to determine the authenticity of that circuit 10.

In some embodiments of the invention, the comparing step may further including determining, using the optical characteristics of each of the PUFs 26, at least one of an ion implant concentration, a quantity of dislocation loops 22, how deep the ions 20 are implanted, how many atoms are implanted, and a size of area of each of the PUFs 26. This information may then be used in the assigning of the values for each of the PUFs. The values assigned to each of the PUFs may cooperatively form a circuit identifier. Thus, the comparing step 506 may include determining if the circuit identifier matches at least one of the groups of values stored in the circuit database 30. As noted above, each of the groups of stored values in the circuit database 30 may be associated with optical characteristics of PUFs of a known authentic circuit.

Finally, the method 500 may include a step of providing an indication of whether or not the integrated circuit 10 is authentic or counterfeit, as depicted in block 508. When each of the values associated with the sensed optical characteristics of the PUFs 26 (i.e., the circuit identifier) match the stored values of at least one of the groups in the circuit database 30, then the controller 34 may audibly or visually indicate that the circuit 10 is authentic. Conversely, when each of the values associated with the sensed optical characteristics of the PUFs 26 (i.e., the circuit identifier) do not match the stored values of at least one of the groups in the circuit database 30, then the controller 34 may audibly or visually indicate that the circuit 10 is a counterfeit. For example, the controller 30 may output authentication information on the visual display device and/or speaker described above to notify the user that the circuit 10 is either authentic or was determined by the controller 30 to be a counterfeit circuit. Alternatively, the controller 34 may only provide audible or visual feedback to the user if the circuit 10 is determined to be authentic or conversely if the circuit 10 is determined to be counterfeit.

Embodiments of the invention described above may be used commercially to prevent counterfeiting of common electronics. It could also be used in defense applications to provide a simple test-and-detect method to ensure a trusted supply chain for critical microelectronic devices. When applied to different semiconductors, such as Si, SiGe, GaAs, and GaN, the implanting of ions could be tailored to that particular material to provide optimum light output when electrically or optically stimulated.

Advantageously, by using ion implants and the associated damage, the PUFs 26 of the present invention require no on-chip power, no complex circuitry, and can thus be used across multiple semiconductor platforms (e.g., Si, GaAs, GaN). Furthermore, because ion implants are a typical and often trivial part of the semiconductor manufacturing process and are buried beneath a surface layer of the integrated circuit 10, it is nearly impossible for competitors or counterfeiters to detect the material PUFs 26 of the present invention. Likewise, small differences in ion implant density are also nearly impossible to detect and even harder to replicate.

Conversely, prior art electrical PUFs could only be used in Si CMOS circuitry, required operation of the integrated circuit to function properly, and thus required fabrication of complex integrated circuitry, making it obvious that the device had been identified as important enough to protect. The prior art electrical PUFs also suffer from reliability issues when heated above 200 degrees Celsius. Advantageously, the material PUFs 26 of the present invention may be reliable up to 500 degrees Celsius, as the recovery process for defects has a very high activation temperature.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A method of reading physically unclonable functions (PUFs) on an integrated circuit, the method comprising:
   electrically or optically stimulating each of the PUFs, wherein the PUFs include high energy ions implanted into crystal lattices of semiconductor material of the integrated circuit at a specific number of areas cooperatively providing a numerical key serving as a unique authentication identifier for the circuit, each area forming one of the PUFs having unique associated damage;
   sensing with an optical sensor optical characteristics of light emitted from the PUFs when electrically or optically stimulated;
   comparing, via a controller, the numerical key with a plurality of stored keys in a circuit database, wherein each of the stored keys are associated with previously-logged optical characteristics of PUFs of at least one known authentic circuit; and
   providing, via the controller, verification of authenticity of the integrated circuit when the numerical key matches one of the stored keys in the circuit database.

2. The method of claim 1, wherein the optical characteristics of the PUFs of the integrated circuit include at least one of wavelength, intensity, and total area of the light received with the optical sensor from each of the PUFs of the integrated circuit.

3. The method of claim 1, wherein the optical characteristics of the PUFs of the integrated circuit are dependent upon at least one of an implant concentration of ions that formed the PUFs, a quantity of dislocation loops of the PUFs, how deep the ions are implanted, how many atoms are implanted in the PUFs, and a size of area of each of the PUFs.

4. The method of claim 1, wherein the step of electrically or optically stimulating includes passing an electric current or strong electric field through each of the PUFs or stimulating photoexcitation of photons in each of the PUFs.

5. The method of claim 1, wherein the semiconductor material may comprise at least one of the following materials: Si, SiGe, GaAs, and GaN.

6. The method of claim 1, wherein the ions implanted into the crystal lattices are at least one of boron and phosphorus.

7. The method of claim 1, further comprising providing, via the controller, an indication that the integrated circuit is a counterfeit circuit when the numerical key does not match one of the stored keys in the circuit database.

8. A method of reading physically unclonable functions (PUFs) on an integrated circuit, the method comprising:
electrically or optically stimulating each of the PUFs, wherein the PUFs include high energy ions implanted into crystal lattices of semiconductor material of the integrated circuit at a plurality of locations by at least one of ion implanters and focused ion beam tools, each location forming one of the PUFs having unique associated damage;
sensing with an optical sensor optical characteristics of light emitted from the PUFs when electrically or optically stimulated, wherein the optical characteristics of the PUFs of the integrated circuit include at least one of wavelength, intensity, and total area of the light received with the optical sensor from each of the PUFs of the integrated circuit;
assigning, via a controller, each of the PUFs a value associated with the optical characteristics of the PUFs based on an algorithm solved with at least one of the optical characteristics or retrieved from a look-up table using at least one of the optical characteristics;
comparing, via the controller, the values associated with the optical characteristics of the PUFs with one or more groups of stored values in a circuit database, wherein each of the groups of stored values are associated with previously-logged optical characteristics of PUFs of at least one known authentic circuit; and
providing, via the controller, audible or visual indication of authenticity of the integrated circuit when each of the values associated with the optical characteristics of the PUFs match the stored values of at least one of the groups in the circuit database.

9. The method of claim 8, further comprising the controller using the optical characteristics of the PUFs of the integrated circuit to determine at least one of an implant concentration of ions that formed the PUFs, a quantity of dislocation loops of the PUFs, how deep the ions are implanted, how many atoms are implanted in the PUFs, and a size of area of each of the PUFs.

10. The method of claim 8, wherein the step of electrically or optically stimulating includes passing an electric current or strong electric field through each of the PUFs or stimulating photoexcitation of photons in each of the PUFs.

11. The method of claim 8, wherein the plurality of locations includes a number of discrete areas, cooperatively providing a numerical key serving as a circuit authentication identifier for the circuit, wherein the comparing step includes comparing the numerical key with a plurality of stored keys in the circuit database.

12. The method of claim 8, wherein the semiconductor material may comprise at least one of the following materials: Si, SiGe, GaAs, and GaN.

13. The method of claim 8, wherein the ions implanted into the crystal lattices are at least one of boron and phosphorus.

14. The method of claim 8, further comprising an audible or visual indication, via the controller, that the integrated circuit is a counterfeit circuit when each of the values associated with the optical characteristics of the PUFs do not match the stored values of at least one of the groups in the circuit database.

15. An authentication apparatus comprising:
a notification device including at least one of a user interface, visual display device, and speaker; and
a controller including a processor and memory, wherein the memory is a non-transitory computer-readable medium with a computer program stored thereon, the computer program comprising:
a code segment for instructing an energy source to electrically or optically stimulate each of a plurality of physically unclonable functions (PUFs) by passing an electric current or strong electric field through each of the PUFs or stimulating photoexcitation of photons in each of the PUFs, wherein the PUFs include high energy ions implanted into crystal lattices of semiconductor material of the integrated circuit at a plurality of locations by at least one of ion implanters and focused ion beam tools, each location forming one of the PUFs having unique associated damage;
a code segment for receiving from an optical sensor optical characteristics of light emitted from the PUFs when electrically or optically stimulated, wherein the optical characteristics of the PUFs of the integrated circuit include at least one of wavelength, intensity, and total area of the light received;
a code segment for comparing values associated with the optical characteristics of the PUFs with one or more groups of stored values in a circuit database, wherein each of the groups of stored values are associated with previously-logged optical characteristics of PUFs of at least one known authentic circuit;
a code segment for commanding the notification device to output an audible or visual indication of authenticity of the integrated circuit when each of the values associated with the optical characteristics of the PUFs match the stored values of at least one of the groups in the circuit database; and
a code segment for commanding the notification device to output an audible or visual indication that the integrated circuit is a counterfeit circuit when each of the values associated with the optical characteristics of the PUFs do not match the stored values of at least one of the groups in the circuit database.

16. The authentication apparatus of claim 15, wherein the computer program further comprises a code segment for determining, based on the optical characteristics of the PUFs of the integrated circuit, at least one of an implant concentration of ions that formed the PUFs, a quantity of dislocation loops of the PUFs, how deep the ions are implanted, how many atoms are implanted in the PUFs, and a size of area of each of the PUFs.

17. The authentication apparatus of claim 15, further comprising the optical sensor communicably coupled with the processor, wherein the optical sensor is configured to sense the optical characteristics of the light emitted from the PUFs when electrically or optically stimulated.

18. The authentication apparatus of claim 15, wherein the memory of the controller further includes the circuit database.

* * * * *

UNITED STATES PATENT AND TRADEMARK OFFICE
CERTIFICATE OF CORRECTION

PATENT NO. : 10,019,565 B2  
APPLICATION NO. : 14/973383  
DATED : July 10, 2018  
INVENTOR(S) : Daniel Jonathan Ewing Page 1 of 1

It is certified that error appears in the above-identified patent and that said Letters Patent is hereby corrected as shown below:

In the Specification

Please insert the following paragraph at Column 1, Line 4:
-- STATEMENT REGARDING FEDERALLY-SPONSORED RESEARCH OR DEVELOPMENT
This invention was made with government support under Contract No.: DE-NA0000622 awarded by the Department of Energy. The government has certain rights in the invention. --

Signed and Sealed this
Tenth Day of September, 2019

Andrei Iancu
*Director of the United States Patent and Trademark Office*